(12) United States Patent
Bhatnagar et al.

(10) Patent No.: US 6,638,912 B2
(45) Date of Patent: *Oct. 28, 2003

(54) PEPTIDE COMPOSITIONS MIMICKING TGF-β ACTIVITY

(75) Inventors: Rajendra S. Bhatnagar, Burlingame, CA (US); Jing Jing Qian, San Bruno, CA (US); Craig Gough, San Francisco, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

This patent is subject to a terminal disclaimer.

(21) Appl. No.: 09/113,696

(22) Filed: Jul. 10, 1998

(65) Prior Publication Data
US 2002/0010134 A1 Jan. 24, 2002

Related U.S. Application Data

(63) Continuation-in-part of application No. 08/742,256, filed on Oct. 31, 1996, now Pat. No. 5,780,436, which is a continuation-in-part of application No. 08/431,954, filed on May 1, 1995, now Pat. No. 5,661,127.

(51) Int. Cl.[7] .................. A61K 38/07; A61K 38/04; A61K 38/05; A61K 38/06; A61K 38/08
(52) U.S. Cl. .................. 514/17; 514/14; 514/15; 514/16; 514/18; 514/19; 530/326; 530/328; 530/329; 530/330; 530/331
(58) Field of Search .................. 514/16, 17, 14, 514/15, 18, 19; 530/329, 326, 328, 330, 331

(56) References Cited

U.S. PATENT DOCUMENTS

| | | | |
|---|---|---|---|
| 5,002,583 A | | 3/1991 | Pitaru et al. |
| 5,055,447 A | | 10/1991 | Palladino et al. |
| 5,158,934 A | | 10/1992 | Ammann et al. |
| 5,171,574 A | | 12/1992 | Kuberasampath et al. |
| 5,178,845 A | | 1/1993 | Constantz et al. |
| 5,208,219 A | | 5/1993 | Ogawa et al. |
| 5,236,905 A | | 8/1993 | Brankovan et al. |
| 5,240,912 A | | 8/1993 | Todaro |
| 5,258,029 A | | 11/1993 | Chu et al. |
| 5,268,455 A | | 12/1993 | Cianciolo |
| 5,270,300 A | | 12/1993 | Hunziker |
| 5,284,763 A | | 2/1994 | Derynk et al. |
| 5,322,933 A | | 6/1994 | Davies et al. |
| 5,324,519 A | | 6/1994 | Dunn et al. |
| 5,354,736 A | * | 10/1994 | Bhatnagar ............ 514/14 |
| 5,364,839 A | | 11/1994 | Gerhart et al. |
| 5,368,858 A | | 11/1994 | Hunziker |
| 5,635,482 A | * | 6/1997 | Bhatnagar ............ 514/14 |
| 5,661,127 A | * | 8/1997 | Bhatnagar et al. ........ 514/16 |
| 5,780,436 A | * | 7/1998 | Bhatnagar et al. ........ 514/18 |
| 5,958,428 A | * | 9/1999 | Bhatnagar ............ 424/400 |

FOREIGN PATENT DOCUMENTS

| | | |
|---|---|---|
| WO | 91/02537 | 3/1991 |
| WO | 93/09228 | 5/1993 |
| WO | 93/09229 | 5/1993 |
| WO | 93/11781 | 6/1993 |
| WO | 96/34881 | 11/1996 |
| WO | 96/38168 | 12/1996 |
| WO | 98/18816 | 5/1998 |

OTHER PUBLICATIONS

Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Archer et al., "Transforming Growth Factor α1: Secondary Structure as Determined by Heteronuclear Magnetic Resonance Spectroscopy," *Biochemistry*, 32, (1993), pp. 1164–1171.
Basler et al., "Control of Cell Pattern in the Neural Tube: Regulation of Cell Differentiation by *dorsalin–1*, a Novel TGFβ Family Member," *Cell*, 73, (May 21, 1993), pp. 687–702.
Berge et al., "Pharmaceutical Salts," *Journal of Pharmaceutical Sciences*, 66:1, (Jan. 1997), pp. 1–19.
Bone et al., "Definitions for Sepsis and Organ Failure and Guidelines for the Use of Innovative Therapies in Sepsis," *Chest*, 101:6 (Jun. 1992), pp. 1644–1655.
Daopin et al., "Crystal Structure of TGF–β2 Refined at 1.8 Å Resolution," *Proteins*, 17, (1993), pp. 176–192.
Hubbell and Langer, "Tissue Engineering," *Chemical and Engineering News*, (Mar. 13, 1995), pp. 42–54.
Massagué, "The Transforming Growth Factor–β Family," *Annu. Rev. Cell. Biol.*, 6, (1990), pp. 597–641.
Termine and Posner, "Calcium Phosphate Formation in vitro: I. Factors Affecting Initial Phase Separation," *Archives of Biochemistry and Biophysics*, 140, (1970), pp. 307–317.

(List continued on next page.)

*Primary Examiner*—David S. Romeo
(74) *Attorney, Agent, or Firm*—Bozicevic, Field & Francis LLP; Carol L. Francis

(57) ABSTRACT

Compositions suitable for pharmaceutical administration are provided in which one compound is a small peptide mimic of TGF-β. More preferably, pharmaceutical compositions of the present invention are formulated as combinations of two components, wherein one component includes a peptide mimic for TGF-β and the other component is structurally or biologically analogous to a small region of collagen and mimics the conformation recognized by collagen binding species. A particularly preferred combination is A-N-V-A-E-N-A (SEQ ID NO:1) and G-T-P-G-P-Q-G-I-A-G-Q-R-G-V-V (SEQ ID NO:17).

19 Claims, 6 Drawing Sheets

OTHER PUBLICATIONS

Termine et al., "Calcium Phosphate Formation in vitro: II. Effects of Environment on Amorphous–Crystalline Transformation," *Archives of Biochemistry and Biophysics*, 140, (1970), pp. 318–325.

Amatayakul–Chantler et al., "[Ser$^{77}$] Transforming Growth Factor–β1," *Journal of Biological Chemistry*, 269:44, (1994), pp. 27687–27691.

Chang et al., "Cartilage–derived Morphogenetic Proteins," *Journal of Biological Chemistry*, 269:45, (1994), pp. 28227–28234.

Chopra et al., "Newly Synthesized Proteoglycans Secreted by Sequentially Derived Populations of Cells from New-–Born Rat Calvaria," *Cell Differentiation and Development*, 32, (1990), pp. 47–59.

Colletta et al., "The Growth Inhibition of Human Breast Cancer Cells by a Novel Synthetic Progestin Involves the induction fo Transforming Growth Factor Beta," *J. Clin. Invest.*, 87, (1991), pp. 277–283.

Galéra et al., "Effect of Transforming Growth Factor–β–1 (TGF–β1) on Matrix Synthesis by Monolayer Cultures of Rabbit Articular Chondrocytes during . . . ," *Experimental Cell Research*, 200 (1992), pp. 379–392.

Grande et al., "Transforming Growth Factor–β1 Induces Collagen IV Gene Expression in NIH–3T3 Cells," *Laboratory Investigation*, 69:4, (1993), pp. 387–395.

Günther et al., "Transforming Growth Factor β1 Regulates Tissue Inhibitor of Metalloproteinases–1 Expression in Differentiated Human Articular Chondrocytes," *Arthritis & Rheumatism*37:3, (1994), pp. 395–405.

Hamilton and Millis, "Developmental Roles for Growth Factor–Regulated Secreted Proteins," *Current Topics in Developmental Biology*, 24, (1990), pp. 193–218.

Li and Drucker, "Growth Facator–like Properties of Parathyroid Hormone–related Peptide in Transfected Rodent Cell Lines," *Cancer Research*, 53, (1993), pp. 2980–2986.

Lynch and Giannobile, "Polypeptide Growth Factors: Molecular Mediator of Tissue Repair," Chapter 33 in *Molecular Pathogenesis of Periodontal Disease*, (1994), pp. 415–425.

Massagué et al., "Multiple Type–β Transforming Growth Factors and Their Receptors," *Journal of Cellular Physiology Supplement*, 5, (1987), pp. 43–47.

Matrisian and Hogan, "Growth Factor–Regulated Proteases and Extracellular Matrix Remodeling during Mammalian Development," *Current Topics in Developmental Biology*, 24, (1990), pp. 219–259.

Nakanishi et al., "Expression of Nerve Growth Factor Family Neurotrophins in a Mouse Osteoblastic Cell Line," *Biochemical and Biophysical Research Communications*, 198:3, (1994), pp. 891–897.

Nogami et al., "Bioassay of Chondrocyte Differentiation by Bone Morphogenetic Protein," *Clinical Orthopaedics and Related Research*, 258, (1990), pp. 295–299.

O'Reilly et al., "Regulation of Expression of Transforming Growth Factor–β2 by Transforming Growth Factor–β Isoforms is Dependent upon Cell Type," *Growth Factors*, 6, (1992), pp. 193–201.

Rosen et al., "Bone Induction and Transforming Growth Factor–β," *Annals New York Academy of Sciences*.

Rutherford et al., "Induction of Reparative Dentine Formation in Monkeys by Recombinant Human Osteogenic Protein–1," *Archs oral Biol.*, 38:7, (1993), pp. 571–576.

Sampath et al., "Recombinant Human Osteogenic Protein–1 (hOP–1) Induces New Bone Formation in Vivo with a Specific Activity Comparable with . . . " *Journal of Biological Chemistry*, 267:28, (1992), pp. 20352–20362.

Saunders and D'Amore, "FGF and TFG–β: Actions and Interactions in Biolgoical Systems," *Critical Reviews in Eukaryotic Gene Expression*, 1:3, (1991), pp. 157–172.

Schwarz et al., "Aberrant TGF–β Production and Regulation in Metastatic Malignancy," *Growth Factors*, 3, (1990), pp. 115–127.

Segarini, Patricia R., "Cell Type Specificity of TGF–β Binding," *Annals New York Academy of Sciences*, 1990; 593: 73–90.

Sporn et al., "Some Recent Advances in the Chemistry and Biology of Transforming Growth Factor–Beta," *Journal of Cell Biology*, 105, (1987), pp. 1039–1045.

Taketazu et al., "Enhanced Expression of Transforming Growth Factor–βs and Transforming Growth Factor–β Type II Receptors . . . ," *Laboratory Investigation*, 70:5, (1994), pp. 620–630.

van Beuningen et al., "Transforming Growth Facator–β1 Stimulates Articular Chondrocyte Proteoglycan Synthesis and Induces Osteophyte Formation . . . ," *Laboratory Investigation*, 71:2, (1994), pp. 279–290.

Wozney et al., "Regulators of Bone Formation: Molecular Clones and Activities," *Science*, 242, (1988), pp. 1528–1534.

Joyce et al., "Role of Transforming Growth Factor–β in Fracture Repair," *Annals New York Academy of Sciences*.

Creighton, T.E., *Proteins: Structures and Molecular Principles*, W.H. Freeman and Company, New York, (1983), pp. 286–287 and 329–333.

* cited by examiner

CONTROL

FIG. 5A

| | | | | | | |
|---|---|---|---|---|---|---|
| 1 | H1 | ACE | 1 | 1.952 | 1.249 | .316 |
| 2 | CH3 | ACE | 1 | 1.927 | 2.333 | .203 |
| 3 | H2 | ACE | 1 | 1.576 | 2.782 | 1.133 |
| 4 | H3 | ACE | 1 | 1.243 | 2.593 | -.605 |
| 5 | C | ACE | 1 | 3.323 | 2.853 | -.119 |
| 6 | O | ACE | 1 | 4.272 | 2.077 | -.210 |
| 7 | N | ALA | 2 | 3.439 | 4.166 | -.310 |
| 8 | HN | ALA | 2 | 2.632 | 4.767 | -.211 |
| 9 | CA | ALA | 2 | 4.695 | 4.857 | -.543 |
| 10 | HA | ALA | 2 | 5.425 | 4.521 | .195 |
| 11 | CB | ALA | 2 | 5.211 | 4.572 | -1.957 |
| 12 | HB1 | ALA | 2 | 4.475 | 4.894 | -2.694 |
| 13 | HB2 | ALA | 2 | 6.142 | 5.115 | -2.122 |
| 14 | HB3 | ALA | 2 | 5.399 | 3.506 | -2.083 |
| 15 | C | ALA | 2 | 4.443 | 6.350 | -.361 |
| 16 | O | ALA | 2 | 3.292 | 6.788 | -.383 |
| 17 | N | ASN | 3 | 5.504 | 7.130 | -.187 |
| 18 | HN | ASN | 3 | 6.426 | 6.699 | -.147 |
| 19 | CA | ASN | 3 | 5.484 | 8.570 | .015 |
| 20 | HA | ASN | 3 | 4.836 | 9.029 | -.733 |
| 21 | CB | ASN | 3 | 4.964 | 8.871 | 1.432 |
| 22 | HB2 | ASN | 3 | 5.670 | 8.464 | 2.158 |
| 23 | HB3 | ASN | 3 | 4.000 | 8.383 | 1.578 |
| 24 | CG | ASN | 3 | 4.760 | 10.357 | 1.704 |
| 25 | OD1 | ASN | 3 | 4.723 | 11.177 | .792 |
| 26 | ND2 | ASN | 3 | 4.654 | 10.739 | 2.969 |
| 27 | HND1 | ASN | 3 | 4.656 | 10.052 | 3.709 |
| 28 | HND2 | ASN | 3 | 4.487 | 11.714 | 3.168 |
| 29 | C | ASN | 3 | 6.925 | 9.054 | -.180 |
| 30 | O | ASN | 3 | 7.816 | 8.242 | -.407 |
| 31 | N | VAL | 4 | 7.196 | 10.354 | -.082 |
| 32 | HN | VAL | 4 | 6.433 | 11.007 | .038 |
| 33 | CA | VAL | 4 | 8.563 | 10.863 | -.110 |
| 34 | HA | VAL | 4 | 9.001 | 10.579 | -1.068 |
| 35 | CB | VAL | 4 | 8.546 | 12.404 | -.038 |
| 36 | HB | VAL | 4 | 7.922 | 12.763 | -.857 |
| 37 | CG1 | VAL | 4 | 7.958 | 12.951 | 1.272 |
| 38 | HG11 | VAL | 4 | 8.590 | 12.684 | 2.119 |
| 39 | HG12 | VAL | 4 | 7.900 | 14.038 | 1.213 |
| 40 | HG13 | VAL | 4 | 6.955 | 12.563 | 1.438 |
| 41 | CG2 | VAL | 4 | 9.949 | 12.988 | -.245 |
| 42 | HG21 | VAL | 4 | 10.376 | 12.608 | -1.174 |
| 43 | HG22 | VAL | 4 | 9.889 | 14.075 | -.306 |
| 44 | HG23 | VAL | 4 | 10.605 | 12.718 | .583 |
| 45 | C | VAL | 4 | 9.414 | 10.217 | .994 |
| 46 | O | VAL | 4 | 10.604 | 9.986 | .807 |
| 47 | N | ALA | 5 | 8.808 | 9.966 | 2.157 |
| 48 | HN | ALA | 5 | 7.829 | 10.176 | 2.244 |
| 49 | CA | ALA | 5 | 9.520 | 9.482 | 3.331 |
| 50 | HA | ALA | 5 | 10.411 | 10.096 | 3.479 |

FIG. 5B

|  |  |  |  |  |  |  |
|---|---|---|---|---|---|---|
| 51 | CB | ALA | 5 | 8.626 | 9.645 | 4.563 |
| 52 | HB1 | ALA | 5 | 7.723 | 9.042 | 4.457 |
| 53 | HB2 | ALA | 5 | 9.169 | 9.314 | 5.450 |
| 54 | HB3 | ALA | 5 | 8.350 | 10.693 | 4.688 |
| 55 | C | ALA | 5 | 9.968 | 8.025 | 3.185 |
| 56 | O | ALA | 5 | 11.076 | 7.684 | 3.587 |
| 57 | N | GLU | 6 | 9.079 | 7.168 | 2.682 |
| 58 | HN | GLU | 6 | 8.245 | 7.512 | 2.233 |
| 59 | CA | GLU | 6 | 9.204 | 5.720 | 2.725 |
| 60 | HA | GLU | 6 | 10.254 | 5.429 | 2.779 |
| 61 | CB | GLU | 6 | 8.456 | 5.210 | 3.964 |
| 62 | HB2 | GLU | 6 | 7.393 | 5.439 | 3.867 |
| 63 | HB3 | GLU | 6 | 8.837 | 5.712 | 4.854 |
| 64 | CG | GLU | 6 | 8.602 | 3.703 | 4.203 |
| 65 | HG2 | GLU | 6 | 9.655 | 3.443 | 4.313 |
| 66 | HG3 | GLU | 6 | 8.176 | 3.138 | 3.375 |
| 67 | CD | GLU | 6 | 7.861 | 3.290 | 5.467 |
| 68 | OE1 | GLU | 6 | 6.706 | 3.745 | 5.612 |
| 69 | OE2 | GLU | 6 | 8.468 | 2.548 | 6.266 |
| 70 | C | GLU | 6 | 8.583 | 5.188 | 1.438 |
| 71 | O | GLU | 6 | 7.633 | 5.781 | .930 |
| 72 | N | ASN | 7 | 9.123 | 4.107 | .882 |
| 73 | HN | ASN | 7 | 9.827 | 3.588 | 1.392 |
| 74 | CA | ASN | 7 | 8.673 | 3.542 | -.382 |
| 75 | HA | ASN | 7 | 7.595 | 3.676 | -.478 |
| 76 | CB | ASN | 7 | 9.390 | 4.236 | -1.545 |
| 77 | HB2 | ASN | 7 | 10.466 | 4.108 | -1.419 |
| 78 | HB3 | ASN | 7 | 9.155 | 5.301 | -1.530 |
| 79 | CG | ASN | 7 | 8.962 | 3.664 | -2.892 |
| 80 | OD1 | ASN | 7 | 7.842 | 3.197 | -3.055 |
| 81 | ND2 | ASN | 7 | 9.840 | 3.699 | -3.887 |
| 82 | HND1 | ASN | 7 | 10.757 | 4.091 | -3.746 |
| 83 | HND2 | ASN | 7 | 9.556 | 3.315 | -4.774 |
| 84 | C | ASN | 7 | 8.974 | 2.049 | -.371 |
| 85 | O | ASN | 7 | 9.950 | 1.634 | .253 |
| 86 | N | ALA | 8 | 8.148 | 1.245 | -1.035 |
| 87 | HN | ALA | 8 | 7.449 | 1.658 | -1.644 |
| 88 | CA | ALA | 8 | 8.215 | -.205 | -1.003 |
| 89 | HA | ALA | 8 | 9.244 | -.529 | -.837 |
| 90 | CB | ALA | 8 | 7.341 | -.717 | .150 |
| 91 | HB1 | ALA | 8 | 6.300 | -.440 | -.024 |
| 92 | HB2 | ALA | 8 | 7.415 | -1.800 | .241 |
| 93 | HB3 | ALA | 8 | 7.675 | -.269 | 1.087 |
| 94 | C | ALA | 8 | 7.762 | -.755 | -2.355 |
| 95 | O | ALA | 8 | 7.562 | -.002 | -3.304 |
| 96 | N | NME | 9 | 7.602 | -2.077 | -2.453 |
| 97 | HN | NME | 9 | 7.783 | -2.641 | -1.638 |
| 98 | CT | NME | 9 | 7.166 | -2.736 | -3.673 |
| 99 | HT1 | NME | 9 | 6.431 | -2.126 | -4.201 |
| 100 | HT2 | NME | 9 | 8.026 | -2.904 | -4.322 |
| 101 | HT3 | NME | 9 | 6.712 | -3.695 | -3.424 |

SEQUENCE LISTING

<160> NUMBER OF SEQ ID NOS: 42

<210> SEQ ID NO 1
<211> LENGTH: 7
<212> TYPE: PRT
<213> ORGANISM: Artificial Sequence
<220> FEATURE:
<223> OTHER INFORMATION: TGF-beta mimic

<400> SEQUENCE: 1

Ala Asn Val Ala Glu Asn Ala
 1               5

<210> SEQ ID NO 2
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 2

Leu Ile Ala Glu Ala Lys
 1               5

<210> SEQ ID NO 3
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 3

Leu Ile Ala Pro Glu Ala
 1               5

<210> SEQ ID NO 4
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (2)...(2)
<223> OTHER INFORMATION: Aib

<400> SEQUENCE: 4

Leu Xaa Ala Glu Ala Lys
 1               5

<210> SEQ ID NO 5
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (3)...(3)
<223> OTHER INFORMATION: X = N-methyl alanine

<400> SEQUENCE: 5

Leu Ile Xaa Glu Ala Lys
 1               5

<210> SEQ ID NO 6
<211> LENGTH: 6
<212> TYPE: PRT

<213> ORGANISM: Artificial Sequence
<220> FEATURE:
<223> OTHER INFORMATION: TGF-beta mimic
<221> NAME/KEY: MOD_RES
<222> LOCATION: (2)...(2)
<223> OTHER INFORMATION: Abu

<400> SEQUENCE: 6

Leu Xaa Ala Glu Ala Lys
 1               5

<210> SEQ ID NO 7
<211> LENGTH: 7
<212> TYPE: PRT
<213> ORGANISM: Artificial Sequence
<220> FEATURE:
<223> OTHER INFORMATION: TGF-beta mimic

<400> SEQUENCE: 7

Gly Gly Gln Ile Ala Asn Ile
 1               5

<210> SEQ ID NO 8
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 8

Glu Gly Ile Ala Gly Lys
 1               5

<210> SEQ ID NO 9
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 9

Leu Ile Ala Asp Ala Lys
 1               5

<210> SEQ ID NO 10
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 10

Leu Ile Ala Asn Ala Lys
 1               5

<210> SEQ ID NO 11
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 11

Leu Ile Ala Glu Ala Ala
 1               5

<210> SEQ ID NO 12

```
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 12

Leu Ile Ala Gln Ala Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 13

Leu Ile Ala Gly Gly Glu
 1               5

<210> SEQ ID NO 14
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 14

Leu Ile Ala Gly Glu Gly
 1               5

<210> SEQ ID NO 15
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 15

Ala Asn Val Ala Glu Lys
 1               5

<210> SEQ ID NO 16
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 16

Leu Ile Ala Lys Gly Lys
 1               5

<210> SEQ ID NO 17
<211> LENGTH: 15
<212> TYPE: PRT
<213> ORGANISM: Artificial Sequence
<220> FEATURE:
<223> OTHER INFORMATION: TGF-beta mimic

<400> SEQUENCE: 17

Gly Thr Pro Gly Pro Gln Gly Ile Ala Gly Gln Arg Gly Val Val
 1               5                  10                  15

<210> SEQ ID NO 18
<211> LENGTH: 6
```

```
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (2)...(2)
<223> OTHER INFORMATION: Aib

<400> SEQUENCE: 18

Ile Xaa Ala Glu Ala Lys
 1               5

<210> SEQ ID NO 19
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (2)...(2)
<223> OTHER INFORMATION: Abu

<400> SEQUENCE: 19

Leu Xaa Ala Glu Ala Lys
 1               5

<210> SEQ ID NO 20
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 20

Leu Pro Ala Glu Ala Lys
 1               5

<210> SEQ ID NO 21
<211> LENGTH: 6
<212> TYPE: PRT
<213> ORGANISM: Artificial Sequence
<220> FEATURE:
<223> OTHER INFORMATION: TGF-beta mimic

<400> SEQUENCE: 21

Leu Ile Pro Glu Ala Lys
 1               5

<210> SEQ ID NO 22
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (3)...(3)
<223> OTHER INFORMATION: Aib

<400> SEQUENCE: 22

Leu Ile Xaa Glu Ala Lys
 1               5

<210> SEQ ID NO 23
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
```

```
<222> LOCATION: (4)...(4)
<223> OTHER INFORMATION: Aib

<400> SEQUENCE: 23

Leu Ile Ala Xaa Glu Ala
 1               5

<210> SEQ ID NO 24
<211> LENGTH: 8
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (7)...(7)
<223> OTHER INFORMATION: bAla

<400> SEQUENCE: 24

Ile Trp Gly Leu Asp Gly Xaa Lys
 1               5

<210> SEQ ID NO 25
<211> LENGTH: 8
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (7)...(7)
<223> OTHER INFORMATION: bAla

<400> SEQUENCE: 25

Trp Ile Ala Leu Glu Gly Xaa Lys
 1               5

<210> SEQ ID NO 26
<211> LENGTH: 9
<212> TYPE: PRT
<213> ORGANISM: Artificial Sequence
<220> FEATURE:
<223> OTHER INFORMATION: Collagen receptor ligands

<400> SEQUENCE: 26

Gly Pro Gln Gly Ile Ala Gly Gln Arg
 1               5

<210> SEQ ID NO 27
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 27

Gln Gly Ile Ala Gly Gln
 1               5

<210> SEQ ID NO 28
<211> LENGTH: 7
<212> TYPE: PRT
<213> ORGANISM: Artificial Sequence
<220> FEATURE:
<223> OTHER INFORMATION: Collagen receptor ligands

<400> SEQUENCE: 28

Gln Gly Ile Ala Gly Gln Arg
 1               5
```

<210> SEQ ID NO 29
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 29

Phe Gly Ile Ala Gly Phe
1               5

<210> SEQ ID NO 30
<211> LENGTH: 5
<212> TYPE: PRT
<213> ORGANISM: Artificial Sequence
<220> FEATURE:
<223> OTHER INFORMATION: Collagen receptor ligands

<400> SEQUENCE: 30

Gly Ile Ala Gly Gln
1               5

<210> SEQ ID NO 31
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 31

Gln Gly Ala Ile Ala Gln
1               5

<210> SEQ ID NO 32
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 32

Phe Gly Ile Ala Gly Phe
1               5

<210> SEQ ID NO 33
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 33

Cys Gly Ile Ala Gly Cys
1               5

<210> SEQ ID NO 34
<211> LENGTH: 6
<212> TYPE: PRT
<213> ORGANISM: Artificial Sequence
<220> FEATURE:
<223> OTHER INFORMATION: Collagen receptor ligands

<400> SEQUENCE: 34

Glu Gly Ile Ala Gly Lys
1               5

```
<210> SEQ ID NO 35
<211> LENGTH: 4
<212> TYPE: PRT
<213> ORGANISM: Artificial Sequence
<220> FEATURE:
<223> OTHER INFORMATION: Collagen receptor ligands
<221> NAME/KEY: MOD_RES
<222> LOCATION: (1)...(1)
<223> OTHER INFORMATION: X = N-acetyl cysteine

<400> SEQUENCE: 35

Xaa Ile Ala Ala
 1

<210> SEQ ID NO 36
<211> LENGTH: 3
<212> TYPE: PRT
<213> ORGANISM: Artificial Sequence
<220> FEATURE:
<223> OTHER INFORMATION: Collagen receptor ligands
<221> NAME/KEY: MOD_RES
<222> LOCATION: (3)...(3)
<223> OTHER INFORMATION: bAla

<400> SEQUENCE: 36

Ile Ala Xaa
 1

<210> SEQ ID NO 37
<211> LENGTH: 4
<212> TYPE: PRT
<213> ORGANISM: Artificial Sequence
<220> FEATURE:
<223> OTHER INFORMATION: Collagen receptor ligands
<221> NAME/KEY: MOD_RES
<222> LOCATION: (1)...(1)
<223> OTHER INFORMATION: X = N-acetyl Cysteine
<221> NAME/KEY: MOD_RES
<222> LOCATION: (4)...(4)
<223> OTHER INFORMATION: X = N-methyl Alanine

<400> SEQUENCE: 37

Xaa Ile Ala Xaa
 1

<210> SEQ ID NO 38
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (3)...(3)
<223> OTHER INFORMATION: X = N-methyl alanine

<400> SEQUENCE: 38

Ile Ile Xaa Glu Ala Lys
 1               5

<210> SEQ ID NO 39
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (3)...(3)
<223> OTHER INFORMATION: X = D-alanine

<400> SEQUENCE: 39
```

```
Leu Ile Xaa Glu Ala Lys
 1               5

<210> SEQ ID NO 40
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (4)...(4)
<223> OTHER INFORMATION: X = D-glutamic acid

<400> SEQUENCE: 40

Leu Ile Ala Xaa Ala Lys
 1               5

<210> SEQ ID NO 41
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (5)...(5)
<223> OTHER INFORMATION: X = D-glutamic acid

<400> SEQUENCE: 41

Leu Ile Ala Pro Xaa Ala
 1               5

<210> SEQ ID NO 42
<211> LENGTH: 6
<212> TYPE: PRT
<213> ORGANISM: Artificial Sequence
<220> FEATURE:
<223> OTHER INFORMATION: TGF-beta mimic
<221> NAME/KEY: MOD_RES
<222> LOCATION: (4)...(4)
<223> OTHER INFORMATION: X = trans-4-hydroxyproline

<400> SEQUENCE: 42

Leu Ile Ala Xaa Ala Lys
 1               5
```

PEPTIDE COMPOSITIONS MIMICKING TGF-β ACTIVITY

CROSS-REFERENCE TO RELATED APPLICATIONS

This application is a continuation-in-part application of U.S. Ser. No. 08/742,256, filed Oct. 31, 1996, U.S. Pat. No. 5,780,436, issued Jul. 14, 1998, incorporated herein by reference, which is a continuation-in-part application of U.S. Ser. No. 08/431,954, filed May 1, 1995, now U.S. Pat. No. 5,661,127, issued Aug. 26, 1997.

FIELD OF THE INVENTION

The invention generally relates to compositions of biologically active components useful for therapeutic applications, such as cancer therapy, and more particularly to compositions including small peptides having (or mimicking) TGFβ, activity and collagen receptor agonists.

BACKGROUND OF THE INVENTION

Cancer is a cellular proliferative disease that is characterized by failure at the level of DNA of normal regulation of growth and/or differentiation. Generally, after an initiating event, there are two stages of the disease. The first is tumorigenesis, the establishment of a cancerous growth. This amplification of cancerous cell populations is supported by increased angiogenesis, which nurtures the growth by enhancing vascular perfusion. Tumorigenesis and angiogenesis seem always to occur together. Later in the natural history of the disease metastasis, in which the cancer spreads to other tissue sites, often occurs. Metastasis results from release and migration of aberrant cells from the primary site of tumorigenesis and their subsequent attachment at distal sites where the processes of tumorigenesis and angiogenesis begin anew.

The major pathobiological processes in tumorigenesis and metastasis can be classified into three categories: cell proliferation leading to cancerous cell amplification and angiogenic cell propagation; integrin-mediated processes of cell attachment and migration, crucial components of both angiogenesis and metastasis; and metalloproteinase-mediated processes that underlie both the release of cancer cells and angiogenesis. Metalloproteinases release aberrant cells from their connective tissue anchorage, facilitating metastatic migration. Angiogenesis depends upon metalloproteinases to clear a path for migrating cells at the advancing capillary front.

Most current approaches to cancer therapy, such as standard chemotherapy and irradiation, are attempts to kill cancer cells. However, the discovery of peptides that inhibit proliferation of cancer cells or inhibit endothelial cell proliferation have raised hopes for new therapeutic modalities. For example, members of the transforming growth factor p family (TGF-β) are among the peptides known to have a number of biological activities related to tumorigenesis (including angiogenesis) and metastasis. TGF-β inhibits the proliferation of many cell types including capillary endothelial cells and smooth muscle cells. TGF-β downregulates integrin expression ($\alpha 1\beta 1$, $\alpha 2\beta 1$, $\alpha\alpha v\beta 3$ involved in endothelial cell migration). Integrins are involved in the migration of all cells, including metastatic ones. TGF-β downregulates matrix metalloproteinase expression needed for both angiogenesis and metastasis. TGF-β induces plasminogen activator inhibitor, which inhibits a proteinase cascade needed for angiogenesis and metastasis. TGF-β induces normal cells to inhibit transformed cells.

Transforming growth factor-βs were originally named for their ability to transform normal fibroblasts to cells capable of anchorage-independent growth. The effects of TGF-βs on cells are generally classified as proliferative and non-proliferative. As originally established with the first experiments on fibroblasts, TGF-βs are bona fide growth factors. Two important cell types in which proliferation is enhanced by TGF-β are osteoblasts and Schwann cells of the peripheral nervous system. However, in many cells, TGF-βs are potent inhibitors of cell proliferation. This negative growth control may be the regulatory mechanism that checks regeneration of certain tissues and may play a role in the initiation of carcinogenesis.

The most important non-proliferative function of TGF-βs are in enhancing the formation of extracellular matrices. Although this is achieved primarily through the increased transcription of both collagen and fibronectin, the inhibition of the proteases from degrading the matrix also contributes to its stability. Degradation of the extracellular matrix is inhibited by the decrease in the secretion of the proteases themselves and the simultaneous increase in the levels of protease inhibitors.

Because of the wide applicability of TGF-βs in clinical therapies, they have been the focus of much research. Although much of the research involved in vitro uses, recent in vivo studies have confirmed some of the more promising in vitro effects.

The natural members of the transforming growth factor-β family range upwards of 25 KDa molecular weight. Clinical uses of growth factors, including TGF-βs, may be limited because of their size, which can cause immune responses. For example, human TGF-β1 is a 25,000 dalton homodimeric protein. In addition to possible adverse immunological responses, large proteins are not often the best candidates for drugs because of the difficulties in administration and delivery.

Consequently, small peptide mimics of a natural growth factor such as TGF-β would be desirable. It would also be advantageous to have small peptides mimicking the biological activity of a large, natural protein such as TGF-β since small peptides on a mole per mole basis would require much smaller net amounts for administration, and topical applications would be more feasible. Also, quite small peptides would tend to have little or no adverse immunological responses, and could be synthesized easily using simple peptide chemistry procedures.

As earlier noted, tumoregenesis and metastasis are integrin-mediated processes of cell attachment and migration. Further, matrix metalloproteinase 1 (MMP-1) processes underlie both the release of cancer cells and angiogenesis. Thus, inhibitors of MMP-1 should interfere with angiogenesis, since it is dependent on the lysis of collagenous matrices in the release of migrating cells in metastasis.

Several recent reports have suggested amelioration of cancer by synthetic versions of endogenous peptides: Cao et al., "Expression of Angiostatin cDNA in a Murine Fibrosarcoma Suppresses Primary Tumor Growth and Produces Long-term Dormancy of Metastases," *J. Clin. Invest.*, 101, (1998), 1055–1063; Boehm et al., "Antiangiogenic Therapy of Experimental Cancer Does Not Induce Acquired Drug Resistance," *Nature*, 390 (1997), 404–407; and Wu et al., "Suppression of Tumor Growth with Recombinant Murine Angiostatin," *Biochem. Biophys. Res. Commun.*, 236(1997), 651–654.

SUMMARY OF THE INVENTION

In one aspect of the present invention, compositions suitable for pharmaceutical administration are provided in which one compound is a small peptide mimic of TGF-β. More preferably, pharmaceutical compositions of the present invention are formulated as combinations of two components, wherein one component includes a peptide mimic for TGF-β and the other component includes compounds that are structurally or biologically analogous to a small region of collagen and mimic the conformation recognized by collagen binding species.

A feature for TGF-β activity believed critical is the peptide's ability to adopt a particular structure, when bound to a TGF-β receptor, that places certain side-chain functional groups in the appropriate relative positions and orientations. The TGF-β mimics of the present invention are sometimes herein referred to as "β-bend peptides," or "extended-bend peptides." The appropriate functional groups are represented, in many cases, within the following initial amino acid sequence, $AA_i$-$AA_{i+1}$-$AA_{i+2}$ wherein $AA_i$ is alanine, asparagine, or leucine, $AA_{i+1}$ is valine or isoleucine, and $AA_{i+2}$ is alanine. Of particular importance is the relatively positioning of the side-chains of $AA_{i+1}$ and $AA_{i+2}$. The correct positioning of these amino acids can be achieved if $AA_{i+1}$ and $AA_{i+2}$ are in either of two backbone conformations: a β-bend or an "extended-bend" conformation with the backbone (φ,Ψ) angles of $AA_{i+1}$ equal to approximately (−60, +135) and those of $AA_{i+2}$ equal to approximately (−60, −45). This sequence is often either immediately followed by or has proximal thereto an amino acid with a hydrogen bond acceptor-containing side-chain. Because the amino acid residue with a hydrogen bond acceptor-containing side-chain does not necessarily have to be immediately followed by, that is adjacent to $AA_{i+2}$, it is referred to as $AA_{i+n}$ where n is an integer equal to or greater than three. If n is greater than 3, then n−3 ("n minus 3") amino acid residues would be between $AA_{i+2}$ and $AA_{i+n}$ in the peptide sequence.

For example, the TGF-β mimics may include the sequence $AA_i$-$AA_{i+1}$-$AA_{i+2}$-$AA_{i+3}$ where $AA_i$ through $AA_{i+2}$ are as before described and $AA_{i+3}$ is an amino acid residue with a hydrogen bond acceptor-containing side-chain (and is glutamic acid, aspartic acid, glutamine, or asparagine). Another example is the sequence $AA_i$-$AA_{i+1}$-$AA_{i+2}$-$AA_{i+3}$-$AA_{i+4}$ where the residue with the hydrogen bond acceptor-containing side-chain is not immediately adjacent, but instead is proximal to, the initial sequence. In this case, $AA_i$ through $AA_{i+2}$ are as before, $AA_{i+3}$ is any suitable amino acid, and $AA_{i+4}$ may be glutamic acid, aspartic acid, glutamine, or asparagine. Yet another example is the sequence $AA_i$-$A_{i+1}$-$AA_{i+2}$-$AA_{i+3}$-$AA_{i+4}$-$AA_{i+5}$. Here, $AA_i$ through $AA_{i+2}$ are as before, $AA_{i+3}$ and $AA_{i+4}$ are suitable amino acids, and $AA_{i+5}$ may be glutamic acid, aspartic acid, glutamine, or asparagine.

The original peptide discovered to have TGF-β activity has been named "cytomodulin" and has the sequence A-N-V-A-E-N-A (SEQ ID NO: 1). Cytomodulin when added to cells in culture in the concentration range $10_{-9}$ to $10_{-6}$ M (1.4 pg/mil to 1400 pg/mil), elicits certain highly specific TGF-β effects in several different cell types. For example, among the effects observed is the inhibition of DNA synthesis in Mv-1-Lu mink lung epithelial cells, the growth and colony formation by NRK-49 F fibroblasts in soft agar, and the induction of increased expression of type I collagen in primary cultures of neo-natal human dermal fibroblasts. Moreover, results with human osteogenic sarcoma (HOS) cell line indicate that cytomodulin also may be a mimic for other members of the TGF-β superfamily, such as bone morphogenic proteins (BMPs) and osteogenic protein (OPs), as evidenced by its ability to specifically stimulate markers (alkaline phosphatase and osteonectin) characteristic of the osteoblast phenotype.

Compositions of the subject invention preferably further include a collagen receptor agonist. Particularly preferred such an agonist binds with high affinity with cell surface receptors for collagen and inhibits the attachment and migration of a variety of cells on collagen. These compounds contain a sequence cleaved by MMP-1, and peptides based upon the sequence contained therein are good substrates of MMP-1. Conformationally-restricted compounds capable of serving as allosteric locks or irreversibly binding ligands for receptors and for MMP-1 have potential for cancer therapy, as they are expected to block the migration of smooth muscle cells and attachment of monocytes and other cells by occupying integrin receptors, and to interfere with angiogenesis within developing tumors by inhibiting the attachment and migration of endothelial cells.

BRIEF DESCRIPTION OF THE DRAWINGS

FIGS. 5A and 5B provide the atomic coordinates for atom numbers 1–101 of the cytomodulin embodiment of the invention.

DESCRIPTION OF THE PREFERRED EMBODIMENTS

Figure 1:
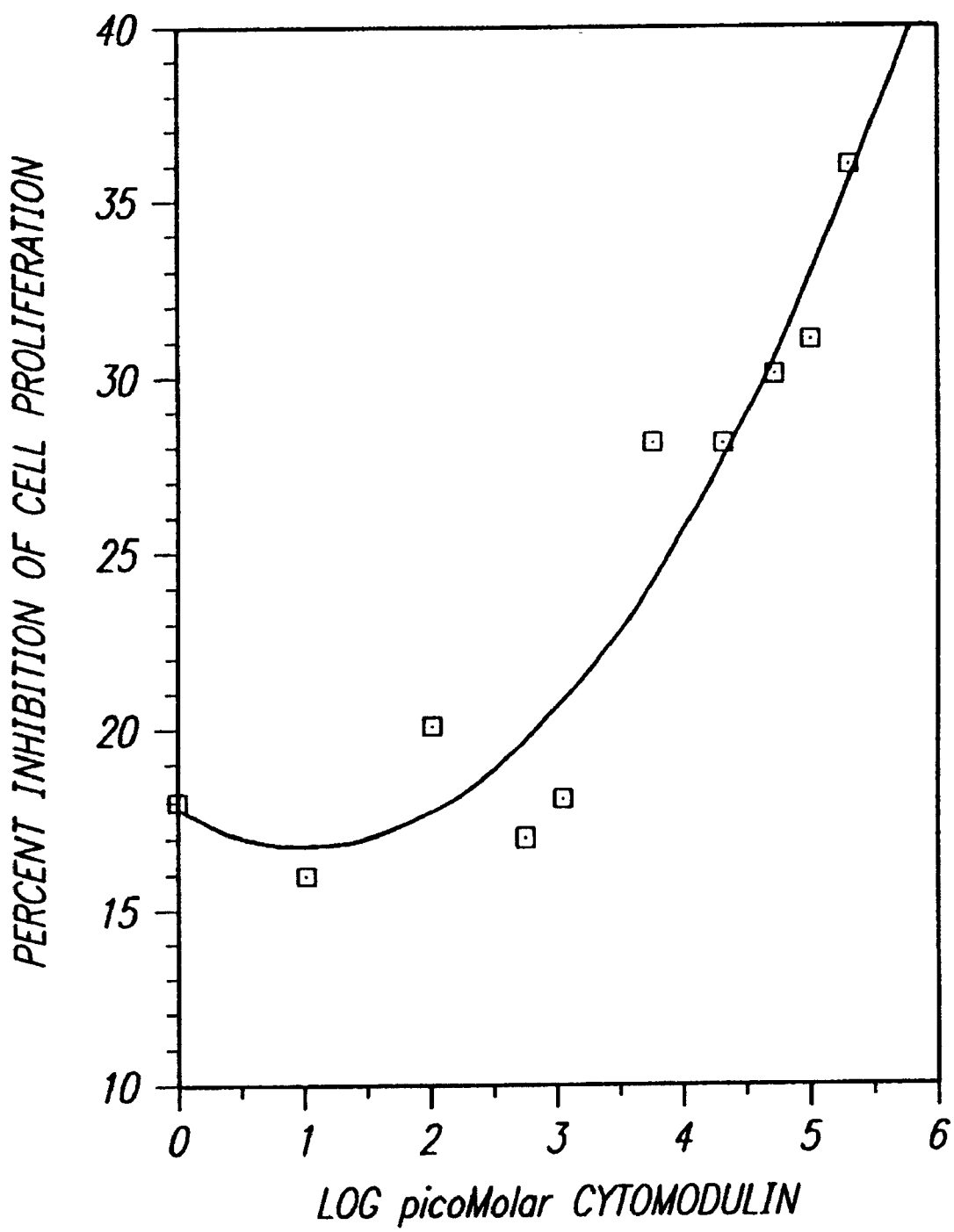
FIG. 1 graphically illustrates the inhibition of DNA synthesis of Mv-1-Lu mink lung epithelial cells by cytomodulin.

Compositions of the invention have various applications, as described, for example, in U.S. Pat. No. 5,780,436 and U.S. Pat. No. 5,354,736, incorporated herein by reference. Cytomodulin and its analogs (that is, TGF-β mimics) are usefull as new components of culture media for use in culturing nerve cells in vitro. These peptides also have utility as a substitute for the natural cytokines in many fields including: in surgery as agents which promote wound healing and regeneration; in orthopedics in promoting bone repair and implant integration; in dentistry in the repair of bony defects and in implant integration; in cancer chemotherapy and in radiation treatment as cytostatic agents for protection of normal stem cells against cell-cycle specific procedures; in treatment of rheumatoid arthritis; in ophthalmology for the treatment of uveitis; as a protective agent for splanchnic artery occlusion reperfilsion injury; and, as reagents for research in the biology of growth factors.

Among the applications particularly contemplated in this application is in cancer therapy for the non-proliferative effects attributable to a TGF-β mimic and for activity as a substrate of MMP-1 for the collagen receptor agonists. In cancer therapy applications, we particularly contemplate use of the inventive compositions as adjuncts to chemotherapy or radiation therapy. Another application contemplated is in treating arteriosclerosis, since the plaques formed within the lumen of blood vessels have been shown to have angiogenic stimulatory activity.

The TGF-β mimics may have the following initial amino acid sequence, $AA_i$-$AA_{i+1}$-$AA_{i+2}$ wherein $AA_i$ is alanine, asparagine, or leucine, $AA_{i+1}$ is valine or isoleucine, and $AA_{i+2}$ is alanine. This sequence is normally either immediately followed by or has proximal thereto an amino acid with a hydrogen bond acceptor-containing side-chain. Because the amino acid residue with a hydrogen bond acceptor-containing side-chain does not necessarily have to be immediately followed by, that is adjacent to $AA_{i+2}$, it is referred to as $AA_{i+n}$ where n is an integer equal to or greater than three. If n is greater than 3, then n−3 ("n minus 3") amino acid residues would be between $AA_{i+2}$ and $AA_{i\ +n}$ in the peptide sequence.

In one embodiment of TGF-β mimics for the invention, n equals three and the amino acid residue with the hydrogen bond acceptor-containing side-chain is thus $AA_{i+3}$. This results in peptides having the following sequence $AA_i$-$AA_{i+1}$-$AA_{i+2}$-$AA_{i+3}$ wherein $AA_i$, $AA_{i+1}$, and $AA_{i+2}$ are as above and $AA_{i+3}$ is glutamic acid, aspartic acid, glutamine, or asparagine. The original peptide with TGF-β activity and an especially preferred embodiment of the present invention, cytomodulin, A-N-V-A-E-N-A (SEQ ID NO: 1) is of this class. Here, $AA_i$-$AA_{i+1}$-$AA_{i+2}$-$AA_{i+3}$ corresponds to the second through fifth residues from the N-terminus of cytomodulin, -N-V-A-E-. Other preferred embodiments are the peptides, L-I-A-E-A-K (SEQ ID NO:2) and L-I-A-E-A-A (SEQ ID NO: 11). In these examples, $AA_i$-$AA_{i+1}$-$AA_{i+2}$-$AA_{i+3}$ corresponds to the first four residues of the peptide, L-I-A-E-.

In another embodiment, n equals four and the amino acid residue with the hydrogen bond acceptor-containing side-chain is thus $AA_{i+4}$. The sequence of the peptides of this class is $AA_i$-$AA_{i+1}$-$AA_{i+2}$-$AA_{i+3}$-$AA_{i+4}$. In this series, $AA_i$, $AA_{i+1}$ and $AA_{i+2}$ are as above, $AA_{i+3}$ is either proline or glycine, and $AA_{i+4}$ is glutamic acid, aspartic acid, glutamine, or asparagine. A preferred embodiment of this class is L-I-A-G-E-G (SEQ ID NO: 14). An especially preferred embodiment is the peptide, L-I-A-P-E-A (SEQ ID NO:3). In both examples, the first five N-terminal amino acids correspond to $AA_i$-$AA_{i+1}$-AA,+2-$AA_{i+3}$-AA,+4.

In yet another embodiment of the present invention, n equals five and the amino acid residue with the hydrogen bond acceptor-containing side-chain is thus $AA_{i+5}$. The sequence of the peptides of this class is $AA_i$-$AA_{i+1}$-$AA_{i+2}$-$AA_{i+3}$-AA, $_{i+4}$-$AA_{i+5}$. In this series, $AA_i$, $AA_{i+1}$, and $AA_{i+2}$ are as above, $AA_{i+3}$ and $AA_{i+4}$ are glycine, and $AA_{i+5}$ is glutamic acid, aspartic acid, glutamine, or asparagine. An especially preferred member of this series is the peptide, L-I-A-G-G-E (SEQ ID NO: 13). In this particular example there is a one to one correspondence between SEQ ID NO:3 and the sequence $AA_i$-$AA_{i+1}$-$AA_{i+2}$-$AA_{i+3}$-$AA_{i+4}$-$AA_{i+5}$.

Collagen analogs of the cell-binding domain of collagen suitable for practicing the present invention, such as in admixtures with the cytomodulin or cytomodulin analogs, are described in U.S. Pat. No. 5,354,736, issued Oct. 11, 1994, inventor Bhatnagar, and U.S. Pat. No. 5,635,482, issued Jun. 3, 1997, inventor Bhatnagar, both incorporated herein by reference. A particularly preferred collagen receptor agonist is sometimes called "P-15" and has the sequence G-T-P-G-P-Q-G-I-A-G-Q-R-G-V-V (SEQ ID NO:17). Collagen analogs described in these patents include Gly-Pro-Gln-Gly-Ile-Ala-Gly-Gln-Arg (SEQ ID NO:26), Gln-Gly-Ile-Ala-Gly-Gln (SEQ ID NO:27), Gln-Gly-Ile-Ala-Gly-Gln-Arg (SEQ ID NO: 28), Phe-Gly-Ile-Ala-Gly-Phe (SEQ ID NO:29), Gly-Ile-Ala-Gly-Gln (SEQ ID NO:30), Gln-Gly-Ala-Ile-Ala-Gln (SEQ ID NO:31), Phe-Gly-Ile-Ala-Gly-Phe (SEQ ID NO:32), Cys-Gly-Ile-Ala-Gly-Cys (SEQ ID NO:33), Glu-Gly-Ile-Ala-Gly-Lys (SEQ ID NO:34), NAc-Ile-Ala-Ala (SEQ ID NO:35), and Ile-Ala-βAla (SEQ ID NO:36), NAc-Ile-Ala-N-Me (SEQ ID NO:37).

The P-15 region represents half of one turn of the collagen triple helix, i.e. fifteen residues, which is believed to be exposed in intact collagen molecules on the surface of fibers. The other half of the turn faces the core of the fiber. Theoretical and experimental studies showed that the sequence contained in P-15 can acquire a conformation dramatically different from the triple helical conformation generally observed in the rest of the collagen molecule. This atypical, or "non-collagen," conformation is believed necessary for recognition by the docking of collagen binding species, such as cell surface receptors for collagen and fibronectin. The three dimensional surface presented by the P-15 region or parts of the P-15 region is complementary to the reactive surface present on the binding species (receptors, fibronectin). Collagen mimics this mimic this surface of collagen.

Peptides of the present invention, both TGF-β mimics and collagen analogs, can be synthesized by various suitable methods that are well known in the art, preferably by solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of a-protecting groups have been described, see Stewart et al. in *Solid Phase Peptide Synthesis* (1984), with the acid labile, urethan-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylamino-propylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

Both the collagen mimics or analogs and some of the TGF-β mimics appear to be β-bend peptides. It is believed that slight amino acid modifications to the β-bend peptide sequences will not affect the peptides' ability to form stable β-bend structures. These modifications include techniques to confer resistance to enzymatic degradation such as adding blocking groups to both the N- and C-terminal residues. Another method for preventing degradation and premature clearance by the renal system is the use of unnatural amino acid substitutes in the peptide sequence. For example, N-methyl-alanine is often substituted for alanine and α-amino isobutryic acid and β-amino butric acid are substitutes for bulky hydrophobic amino acids. Yet another technique is replacing the L-amino acid residue in the peptide sequence with a D-amino acid counterpart. For example, an alanine may be replaced with D-alanine.

Monoclonal or polyclonal antibodies and non-peptide analogs that can be designed to mimic the effects of the peptides, are also contemplated. The polyclonal or monoclonal antibodies may be raised in rabbits, mice, or other animals or tissue cultured cells or can be products of cells of human origin. They may also be produced of recombinant DNA technology either in a form identical to that of the native antibody or as chimeric molecules, constructed by recombination of antibody molecules of man and animal origins or in other forms chosen to make the antibodies most suitable for use in therapy. Further, the replacement of amino acid residues and the amide forms (at the C terminus) for analogues are known.

Therapeutic compositions of this invention will be formulated depending upon the effective doses required and the modes of administration used. For example, pharmaceutical compositions can be formulated where the TGF-β mimic, whether by itself or in combination with the collagen analog, is in an amount of from 1 μg/kg to 10 mg/kg of patient weight. As a general proposition, the total pharmaceutically effective amount of each peptide administered will be subject to a great deal of therapeutic discretion. The composition embodiments as therapeutic agents are administered to the patient by any suitable technique, such as by continuous infusion or bolus infusion. The compositions to be used in the inventive therapy will be formulated and dosed in a fashion consistent with good medical practice, taking into account the clinical condition of the individual patient, the method of administration, the scheduling of administration, and other facts known to practitioners. The "effective amount" for purposes described herein is thus determined by such considerations.

Particularly contemplated are systemic administrations, intravenous administration, subcutaneous administration, intra-peritoneal injection, sub-periosteal injection, intra-tracheal administration, release from polymers or pumps, implants, or release from liposomes. Suitable implants (if using an implanted device) include, for example, gel foam, wax, or microparticle-based implants. Doses used should be sufficient to achieve circulating plasma concentrations of active ingredient that are efficacious. Effective doses may be extrapolated from dose-response curves derived from in vitro or animal model test systems.

When a β-bend or extended-bend peptide is prepared for administration by mixing with physiologically acceptable carriers, i.e., carriers which are non-toxic to recipients at the dosages and concentrations employed, this will normally entail combining the inventive peptide(s) with buffers, antioxidants such as ascorbic acid, low molecular weight (less than about 10 residues) polypeptides, proteins, amino acids, carbohydrates including glucose or dextrins, chelating agents such as EDTA, and other excipients. When used in therapeutic administrations, the components must be sterile. This is readily accomplished by filtration through sterile filtration (0.22 micron) membranes.

The β-bend or extended-bend peptides may be administered in any pharmacologically acceptable carrier, and depending upon the desired mode of administration, may be formulated along with liquid carrier into liposomes, microcapsules, polymers or wax-based and controlled release preparations, or be formulated into tablet, pill, or capsule forms.

The peptides form pharmaceutically acceptable salts with organic and inorganic acids and can be administered in salt form can be amidated. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzene-sulfonic, methane- and ethanesulfonic, hydroxymethane- and hydroxyethane-sulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methyl-glucosamine; N-methylglucamine; L-glutamine; N-methylpiperazine; morpholine; ethylenediamine; N-benzyl-phenethylamine; tris(hydroxymethyl)aminomethane; and the like. (See, for example, "Pharmaceutical Salts," *J. Pharm. Sci.,* 66(1), 1–19 (1977).)

Therapeutic formulations containing at least one β-bend or extended-bend peptide may be prepared for storage by mixing with optional physiologically acceptable carriers, excipients or stabilizers, in the form of lyophilized cake or aqueous solutions. Acceptable carriers, excipients or stabilizers are nontoxic to recipients at the dosages and concentrations employed when administered, and include buffers such as phosphate, citrate, and other organic acids; antioxidants including ascorbic acid; low molecular weight (less than about 10 residues) polypeptides; proteins, such as serum albumin, gelatin or immunoglobulins.

Other components can include glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, PLURONICS or PEG.

Compositions may be used in the form of a sterile irrigant, preferably in combination with a physiological saline solution. Compositions for systemic administration preferably are formulated as sterile, isotonic parenteral injections or infusions.

Biological activities of the inventive peptides will now be further illustrated by the following examples, which are intended to be illustrative and not limiting.

EXAMPLE 1

Inhibition of DNA Synthesis of Mv-1-Lu Mink Lung Epithelial Cells

The effect of TGF-β and cytomodulin were evaluated by determining the rate of [$^1$H]thyidine incorporation into total acid-insoluble DNA and cell number. See generally, Sampath et al., *Journal of Biological Chemistry*, 267, pp. 20352–20362 (1992). DNA synthesis rates were determined in triplicate cultures after 24 hour treatment with various concentrations ($10-9$ M to $10^{-6}$M) of either TGF-β or cytomodulin (which was synthesized by the Merrifield method) by adding [methyl-$^3$H]thymidine (2 μCi/ml, 80 Ci/mmol) for 6 hours before the termination of the culture. Incorporation was terminated by aspiration of the medium, and after washing three times with phosphate-buffered saline, the trichloroacetic acid (10%)-precipitated radioactive DNA was extracted with 1.0% (w/v) sodium dodecyl sulfate, 0.1 M NaOH and quantitated by liquid scintillation counting. For cell number determination, $1 \times 10^5$ cells were plated in flasks in MEM containing 10% FBS, and after 24 hours, the growth medium was replaced with serum-free medium containing various conceptions of TGF-β and cytomodulin. Triplicate cultures were harvested every 24 hours for the duration of 7 days, and the cell number was determined by counting cells released by trypsin digestion in a fixed volume hemacytometer.

The growth inhibition curve for cytomodulin were similar to that observed for TGF-β at the same concentration range.

EXAMPLE 2

Growth and Colony Formation by NRK-49 F Fibroblasts in Soft Agar

The original assay for TGF-β, the ability to promote anchorage independent growth of normal fibroblasts is still one of the hallmarks of TGF-β activity. NRK-49 F fibroblasts were grown at 37° C. in DEM supplemented with 10% fetal calf serum. The experiments were performed with culture medium, 10 ng/mg epidermal growth factor (EGF), and 10 ng/ml platelet-derived growth factor (PDGF); however, unlike TGF-β, which does not induce colony formation in the absence of these factors (see, for example, Massagu, *J. Biol. Chem.*, 259, pp. 9756–9761 (1984)), cytomodulin did induce colony formation without these two growth factors. To this, either 100 nM TGF-β (positive control) or 100 nM cytomodulin was added. NRK49 F fibroblasts ($5 \times 10^4$ cells/ml) were mixed with 0.3% agar were plated on the bottom of 35 mm culture dishes. Colony formation was observed starting on day 3 of culture.

As expected no colonies were formed in those cultures containing only the basic medium. Also, as expected, colonies with TGF-β grew colonies. Surprisingly, the cytomodulin cultures also formed colonies to approximately the same extent as the TGF-β cultures. The growth characteristics of the colonies over time were similar between TGF-β and cytomodulin cultures.

Figure 2A:
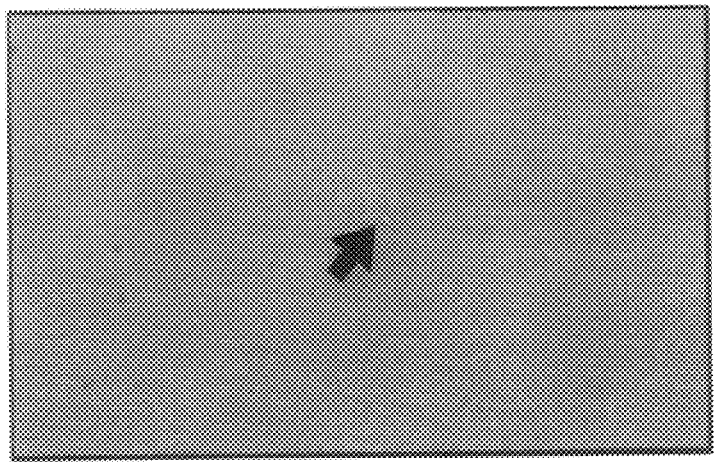
FIG. 2 are photomicrographs (magnification 500 times) wherein Panel (A) is a control, Panel (B) is with 100 nM cytomodulin, and Panel (C) is 100 nM cytomodulin plus EGF and PDGF, all five days in soft agar with NRK-49 F normal rat kidney fibroblasts.
Figure 2B:
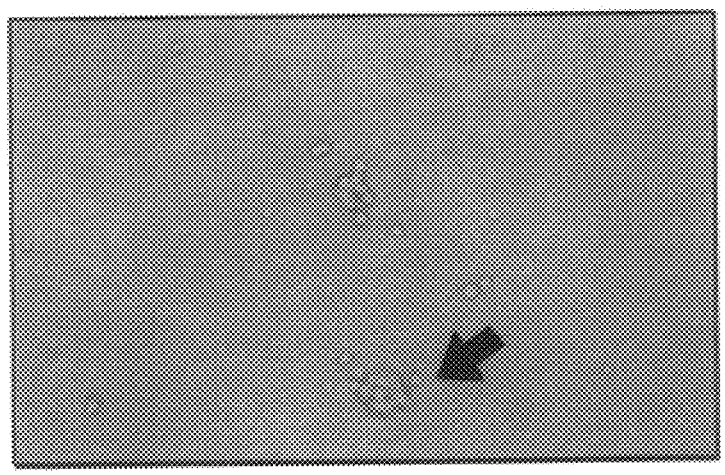
Figure 2C:
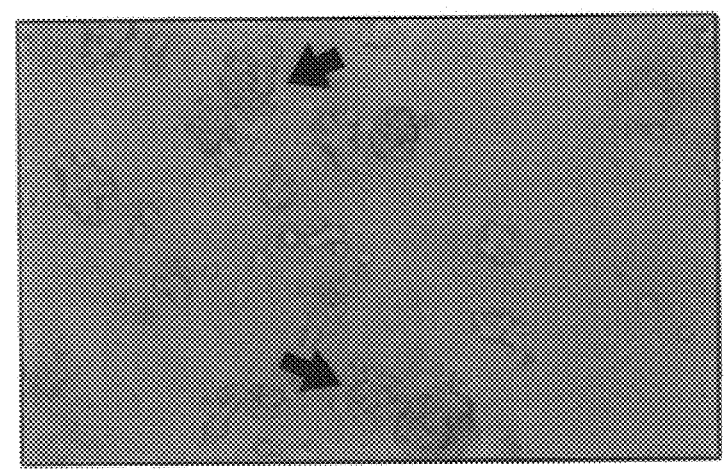
Figure 3A:
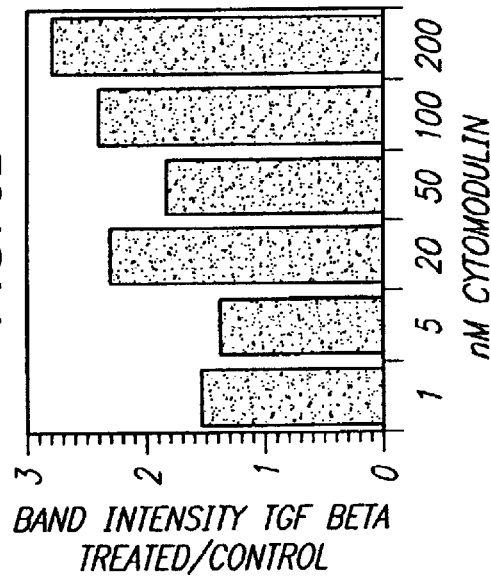
FIG. 3 graphically illustrates the modulation of gene expression in HOS cells by cytomodulin, where Panels (A), (B), and (D) show increased expression while Panel (C) modulated activity depending on concentration, which is however quite characteristic of TGF-β in cells.
Figure 3B:
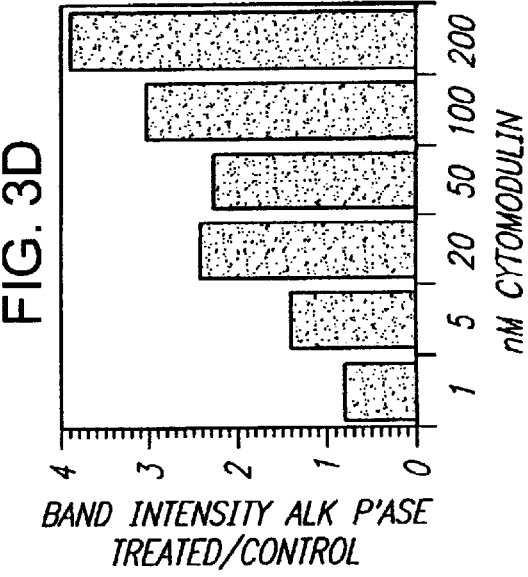
Figure 3C:
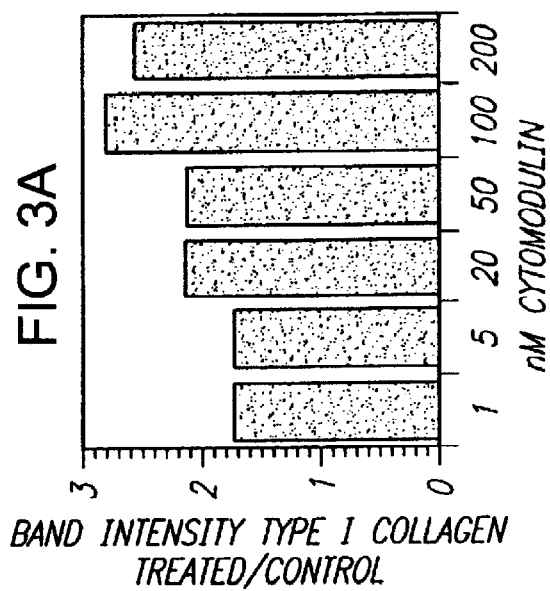
Figure 3D:
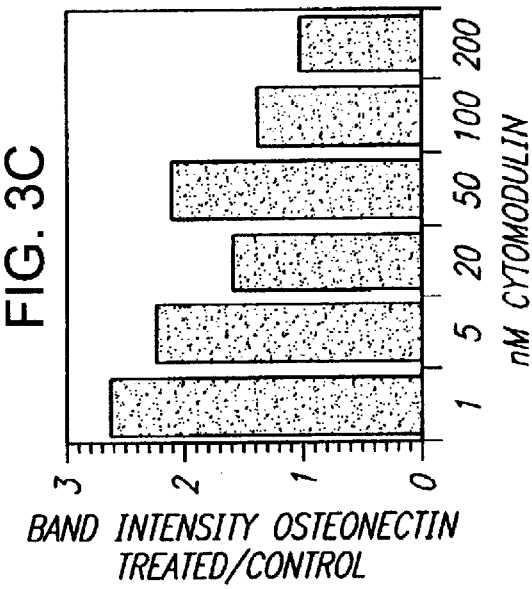
Figure 4A:
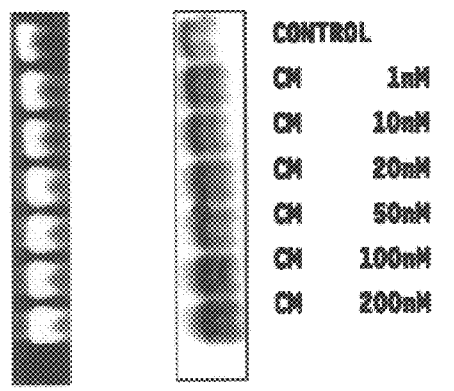
FIG. 4 having panels (A) through (D) are Northern Blots corresponding to the data graphically illustrated by FIG. 3 and its respective panels, (A)–(D)
Figure 4B:
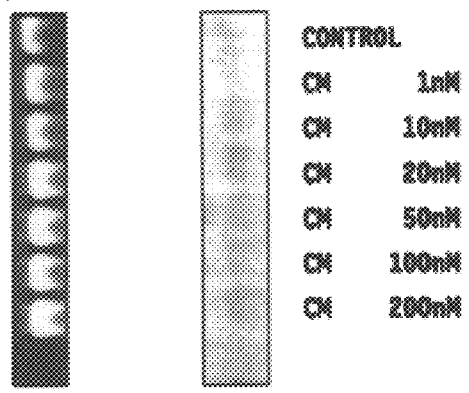
Figure 4C:
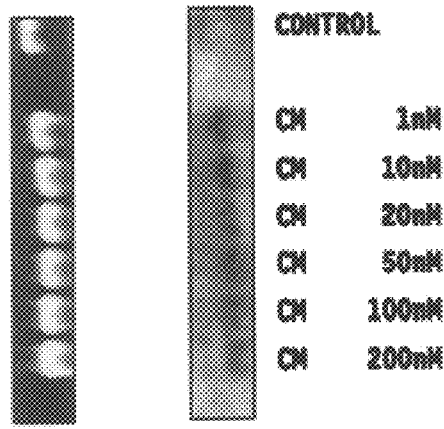
Figure 4D:
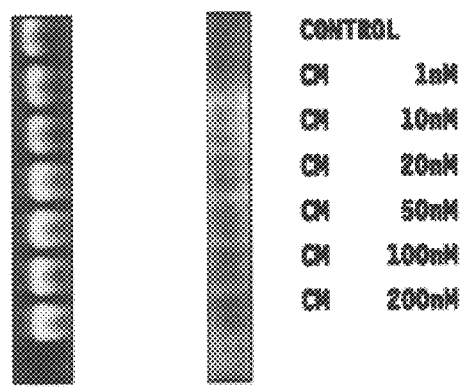

With reference to FIG. 2, photomicrographs are illustrated that were taken on day 5 of the fibroblast culturing. Colony formation was actually observed starting on day 3 of culture. As seen in FIG. 2(A), few cells survived culture in the absence of any growth factors. FIG. 2, Panel (B) and Panel (C) show the formation of small colonies (arrows) in the presence of cytomodulin, with Panel (C) also including EGF and PDGF, which induced much larger colonies (arrows). This is analogous to the induction of colony formation by TGF-β, except that TGF-β requires the concomitant presence of epidermal growth factor (EGF) and platelet derived growth factor (PDGF); however, as seen by Panel (B), cytomodulin did induce colony formation by itself

EXAMPLE 3

RNA Isolation and Northern Analysis

Total cellular RNA was isolated using essentially the method described by Maniatis. Sambrook et al., *Molecular Cloning: A Laboratory Manual*, Cold Spring Harbor Laboratory Press, Second Edition (1989). Cells were lysed with 0.5% SDS and 0.1 potassium acetate. The lysate was extracted with phenol and centrifuiged at 5000 rpm for 15 minutes. The aqueous phase was precipitated with 2 volumes ethanol in 0.1 M Tris, pH 8.0 and 0.2 M NaCl. The pellet was resuspended and quantitated by measuring the ultraviolet absorbance at 260 nm. RNA purity was assessed by comparing the ultraviolet absorbance at 260 inm with that at 280 nm.

RNA (10 μg/lane) was electrophoresed at 3 to 4 v/cm through a 0.7% agarose, 2.2 M formaldehyde denaturing gel. RNA was transferred by capillary transfer to nylon membranes. RNA integrity, gel loading, and transfer efficiency were assessed by methylene blue stained 28S and 18 S bands. The filters were baked at 80° C. for 2 hours to immobilize the RNA. After baking, the filters were hybridized at 65° C. in 0.5 M NaPO$_4$ buffer, pH 7.0, containing 1 mM EDTA, 7% sodium dodecyl sulfate, and 1% bovine serum albumin. cDNA probes were labeled with DDIG (fluorescent probe) by the random primer method, using Klenow enzyme. Hybridization for 18 hours at 65° C. followed by washing, was performed.

Data were analyzed by scanning digoxigenin-dVTP according to manufacturer's procedure (Boehringer Mannheim Biochemica, DIG DNA labelling kit, Cat. No. 1175033).

EXAMPLE 4

Stable α-Bend and TGF-β Activity

FIGS. 5A and 5B show the atomic coordinates of the bioactive structure of cytomodulin (atoms 1–101). Thus, the structure represented by FIGS. 5A and 5B, describes the β-bend that is one of the possible structures consistent with TGF-β activity. Without being limited by theory, if the structure-activity model is correct, analogs having substantially the same structure as cytomodulin will also exhibit TGF-β like activity. Similarly, by exploiting allosteric binding mechanisms, compounds may be synthesized with increased or decreased activity with respect to cytomodulin.

EXAMPLE 5

Using the three dimensional structure of cytomodulin (FIGS. 5A and 5B) as a guide, two initial cytomodulin analogs were designed. From studying the structure, the key features appeared to be the -V-A- sequence responsible for the stable β-bend or extended-bend conformation and a side-chain possessing a hydrogen bond acceptor shortly thereafter. At this point, the working structure-activity profile was:

(1) a hydrophobic or neutral amino acid at position i;
(2) a branched hydrophobic at position i+1;
(3) a small aliphatic at position i+2, where positions i+1 and i+2 together form the β-bend structure; and
(4) a side-chain possessing a hydrogen bond acceptor shortly thereafter at either i+3 or i+4 if i+3 is a proline.

To test this hypothesis, two cytomodulin analogs, L-I-A-E-A-K (SEQ ID NO: 2 or L2) and L-I-A-P-E-A (SEQ ID NO:3 or L1) were synthesized and tested. In both peptides, -V-A- was replaced by -I-A- and the first two N-terminal amino acid sequence of cytomodulin was replaced with leucine. In SEQ ID NO:2, glutamic acid is at position i+3 since it is the first side-chain after the β-bend structure. In SEQ ID NO:3, proline is at position i+3. Since proline does not have a "side-chain," the glutamic acid was placed at position i+4.

Both cytomodulin analogs, L1 and L2, displayed at least as much TGF-β like activity as cytomodulin. They promoted the growth of NRK-49F cells in soft agar and inhibited the proliferation of MV-1-Lu cells. They increased the expression of type I collagen and TGF-β and decreased the expression of collagenase in human dermal fibroblasts. Moreover, as with cytomodulin, L1 and L2 also increased the expression of type I collagen, TGF-β and alkaline phosphatase in HOS cells.

EXAMPLE 6

Analogs of SEQ ID NO:2 and SEQ ID NO:3 were made to further probe the sequence requirements for TGF-β like activity. To that end, the following peptides were made:

L-(Aib)-A-E-A-K (SEQ ID NO:4)
L-I-(Nme-A)-E-A-K (SEQ ID NO:5)
L-(Abu)-A-E-A-K (SEQ ID NO:6)
G-G-Q-I-A-N-I (SEQ ID NO:7)
E-G-I-A-G-K (SEQ ID NO:8)
L-I-A-D-A-K (SEQ ID NO:9)
L-I-A-N-A-K (SEQ ID NO: 10)
L-I-A-E-A-A (SEQ ID NO: 11)
L-I-A-Q-A-K (SEQ ID NO: 12)
L-I-A-G-G-E (SEQ ID NO:13)
L-I-A-G-E-G (SEQ ID NO: 14)
A-N-V-A-E-K (SEQ ID NO: 15)
L-I-A-K-G-K (SEQ ID NO: 16)

Of the non-standard amino acids, Aib is α-amino isobutyric acid, Nme-Ala is N-methyl alanine and Abu is α-amino butyric acid.

SEQ ID NOs:4–6, which are minor variants of SEQ ID NO:2, mimicked the biological activities of TGF-β and cytomodulin as shown by the inhibition of the proliferation of Mv-1-Lu epithelial cells and increased expression of collagen I and TGF-β in HOS cells. Sample thymidine incorporation data for SEQ ID NOs:4–6 are shown in Table 1.

TABLE 1

Inhibition of Incorporation of $^3$H-thymidine in
MV-1 Lu cells in the Presence of Test Peptides

| Control (No peptides added) | $^3$H-Radioactivity, $10^3$ dpm (% Inhibition) |
|---|---|
|  | 3.57 (–) |
| (IV) LAibAEAK (SEQ ID NO:4) | |
| 1 mM | 2.60 (27%) |
| 5 nM | 2.31 (35%) |
| 50 nM | 1.94 (46%) |
| 100 nM | 1.44 (60%) |
| 500 nM | 1.61 (55%) |
| (V) LINmeAEAK (SEQ ID NO:5) | |
| 1 nM | 1.61 (47%) |
| 5 nM | 1.76 (42%) |
| 50 nM | 1.60 (41%) |
| 100 nM | 1.81 (40%) |
| 500 nM | 1.42 (53%) |
| (VI) LAbuAEAK (SEQ ID NO:6) | |
| 1 nM | 2.02 (33%) |
| 5 nM | 1.97 (35%) |

However, SEQ ID NOs:7–8 did not display significant TGF-β activity. This was not unexpected given the working model. An amino acid with a negatively charged side-chain is not present in SEQ ID NO:7. Although a glutamic acid is present in SEQ ID NO:8, it is on the N-terminal side of the β-bend and not on the C-terminal side as with cytomodulin, L1, and L2.

Inhibition of $^3$H-thymidine incorporation results for SEQ ID NOs:9–16 are shown in Table 2. The numbers shown at the various concentration are the ratio of the inhibition rate of the peptide being tested over the inhibition rate of cytomodulin (SEQ ID NO: 1) at the same concentration. Because cytomodulin inhibits the proliferation of MV-1-Lu cells at least as much as TGF-β, cytomodulin and not TGF-β was used as a control.

TABLE 2

Growth Inhibition Activity of Inventive Peptides

| | | Inhibition in comparison to cytomodulin (Inhib by new peptide/Inhib by cytomodulin) Concentration (nM) | | | |
|---|---|---|---|---|---|
| Peptide Composition | SEQ ID NO | 1 | 10 | 100 | 1000 |
| LIADAK | SEQ ID NO:9 | 0.45 | 0.87 | 1.14 | 1.25 |
| LIANAK | SEQ ID NO:10 | 1.70 | 2.00 | 1.43 | 3.05 |
| LIAEAA | SEQ ID NO:11 | 1.16 | 1.00 | 1.17 | 1.85 |
| LIAQAK | SEQ ID NO:12 | 0.90 | 1.10 | 0.80 | 1.56 |
| LIAGGE | SEQ ID NO:13 | 1.10 | 1.33 | 1.45 | 1.90 |
| LIAGEG | SEQ ID NO:14 | 0.66 | 0.85 | 1.41 | 1.88 |
| ANVAEK | SEQ ID NO:15 | — | 0.80 | 1.00 | — |
| LIAKGK | SEQ ID NO:16 | — | 0.65 | 0.67 | — |

As illustrated by Table 2, all peptides with sequences represented by SEQ ID NOs:9–16 inhibited at least some amount of thymidine uptake. From these results, the general model for preparing peptides with TGF-β activity appears to work surprisingly well.

One peptide in particular is especially noteworthy. SEQ ID NO: 10, L-I-A-N-A-K, inhibited the proliferation of Mv-1-Lu epithelial cells even more than cytomodulin at every concentration tested. Because SEQ ID NO: 10 does not contain a negatively charged side-chain, the working model clearly had to be redefined to incorporate a generalized hydrogen bond acceptor rather than a negative charge. Based upon the inhibition activities of both SEQ ID NOs: 10 and 12 where asparagine and glutamine replaced glutamic acid, the carbonyl group (C=O) appears to be the critical feature and not necessarily the entire carboxylic acid group (COO—).

Another interesting set of peptides is SEQ ID NOs:13–14 which explore the positional requirements of the carbonyl group as a hydrogen bond acceptor. The activities of these peptides appear to be the result of the unusual flexibility of the glycine backbone. Because glycine's backbone may sample virtually all allowable torsional angles, a carbonyl group as a hydrogen bond acceptor placed proximal to the α-bend or extended-bend structure with (φ,Ψ) angles equal to (–60, +135) for $AA_{n+1}$ and $AA_{n+2}$, respectively, could attain its necessary conformation without incurring a significant energy cost. Since SEQ ID NO: 13 would be more flexible than SEQ ID NO: 14, it is not surprising that SEQ ID NO: 13 inhibits thymidine uptake more than SEQ ID NO: 14.

Another noteworthy feature includes SEQ ID NO: 11. Since this peptide displays at least as much activity as cytomodulin, the C-terminal lysine of L1 and L2 are clearly not important. As a result, the structure activity relationship required for TGF-β activity appears to be:

(1) a hydrophobic or neutral amino acid at position i;

(2) a branched hydrophobic at position i+1 (i.e. Val, Ile);

(3) a small aliphatic at position i+2 (i.e. Ala), where positions i+1 and i+2 together form the critical U-bend structure; and (4) a side-chain containing a hydrogen-bond acceptor shortly thereafter.

EXAMPLE 7

Tests for bioactivity were conducted as described above for DNA inhibition.

In summary, the cytomodulin analogs listed in Table 3 were all found active as agonists.

TABLE 3

| SEQUENCE | SEQUENCE SYMBOL | SEQ ID NO: |
|---|---|---|
| Ala-Asn-Val-Ala-Glu-Asn-Ala | A-N-V-A-E-N-A | 1 |
| Leu-Ile-Ala-Pro-Glu-Ala | L-I-A-P-E-A | 3 |
| Leu-Ile-Ala-Glu-Ala-Lys | L-I-A-E-A-K | 2 |
| Ile-Aib-Ala-Glu-Ala-Lys | I-(Aib)-A-E-A-K | 18 |
| Ile-(Ile)-(Nme-Ala)-Glu-Ala-Lys | I-(I)-(NMeA)-E-A-K | 38 |
| Leu-(Abu)-Ala-Glu-Ala-Lys | L-(Abu)-A-E-A-K | 19 |
| Leu-Ile-Ala-Asn-Ala-Lys | L-I-A-N-A-K | 10 |
| Leu-Ile-Ala-Glu-Ala-Ala | L-I-A-E-A-A | 11 |
| Leu-Ile-Ala-Lys-Gly-Lys | L-I-A-K-G-K | 16 |
| Leu-Pro-Ala-Glu-Ala-Lys | L-P-A-E-A-K | 20 |
| Leu-Ile-Pro-Glu-Ala-Lys | L-I-P-E-A-K | 21 |
| Leu-Ile-(Aib)-Glu-Ala-Lys | L-I-(Aib)-E-A-K | 22 |
| Leu-Ile-(D-Ala)-Glu-Ala-Lys | L-I-(D-Ala)-E-A-K | 39 |
| Leu-Ile-Ala-(D-Glu)-Ala-Lys | L-I-A-(D-Glu)-A-K | 40 |
| Leu-Ile-Ala-(Aib)-Glu-Ala | L-I-A-(Aib)-E-A | 23 |
| Leu-Ile-Ala-Pro-(D-Glu)-Ala | L-I-A-P-(D-Glu)-A | 41 |
| Leu-Ile-Ala-(X$_1$)-Ala-Lys | L-I-A-(X$_1$)-A-K | 42 |
| Ile-Trp-Gly-Leu-Asp-Gly-bAla-Lys | I-W-G-L-D-G-(bAla)-K | 24 |
| Trp-Ile-Ala-Leu-Glu-Gly-bAla-Lys | W-I-A-L-E-G-(bAla)-K | 25 |

(Abu) = α-amino butyric acid
(Aib) = α-amino isobutyric acid
(NmeA) = N-methyl alanine
X$_1$ = trans-4-hydroxyproline As seen by Table 3, L-I-P-E-A-K (SEQ ID NO:21) is active as an agonist. Thus, the φ value at position 3 must be negative, and the Ψ value at position 2 must be positive. This is consistent with the activity of a cytomodulin tested earlier containing N-methyl-alanine in position 3, since the N-methyl-alanine would also enforce a positive ω value at position 2. (φ, Ψ) for this conformation are likely approximately (−60, +135) (in degrees), with a large degree of variation possible.

L-I-[Aib]-E-A-K (SEQ ID NO:22) is also active as an agonist. This, together with the activity of LIPEAK (SEQ ID NO:21) and the derivative with N-methyl-alanine in position 3, indicates a right-handed α-helical conformation at position 3. (φ, Ψ) for this conformation are approximately −60, −45, (with a large degree of variation possible).

L-I-[D-Ala]-E-A-K is also active as an agonist. This serves as a further confirmation of the result for SEQ ID NO:22 and its structural interpretation.

To summarize the results for the derivatives of the LIAEAK (SEQ ID NO:2) peptide: (1) Position 2 must adopt a conformation in which φ<0 and Ψ>0; i.e., a conformation in the upper left corner of the Ramachandran map, with (φ, Ψ) approximately (−60, +135); (2) position 3 must adopt a negative value of φ, and is likely in a right-handed a-helical conformation, in which (φ, Ψ) are approximately (−60, −45).

Since Aib, Pro, and N-methyl-Ala at position 3 all resulted in active peptides when they were placed in position 3 of the LIAEAK (SEQ ID NO:2) derivatives, the conformation at this position must be energetically reasonable for all three of these amino acids. This suggests that the amino acid at this position is in a right-handed ca-helical conformation. This conformation is the global energy minimum of an Aib residue, and a good energy minimum for a Pro residue. It is a bit high in energy for an N-methyl-Ala residue. However, there is no alternative to the right-handed a-helical conformation for this position, since although the proline low-energy region for which φ<0 and Ψ>0 overlaps with a stable region of the N-methyl-alanine Ramachandran map, this region of common low energy for both Pro and N-methyl-Ala does not overlap with a low-energy region of the Aib Ramachandran map. Aib has a region of low energy for which φ<0 and Ψ>0, but it has a less negative value of φ than the nearby region for N-methyl-Ala and Pro; it does not overlap with the N-methyl-Ala and Pro areas of low energy.

The bioactive conformation derived for LIAEAK (SEQ ID NO:2) and its derivatives above matches, in terms of its surface topography, a region of somewhat different amino acid sequence in the NMR structure of TGF-β (Hinck et al., (1996) *Biochemistry*, 35, 8517–8534). The region of TGF-β-1 that is part of a 25-residue polypeptide has been found to bind to TGF-β receptors (Huang et al., (1997) *J. Biol. Chem.*, 272, 27155–27159).

Thus, LIAEAK (SEQ ID NO:2) can have positions 2 and 3 (Ile and Ala) in conformations consistent with the (φ, ω) restrictions discussed above for the biologically active structure.

Although the topology (sequence) is different for LIAEAK (SEQ ID NO:2) and the corresponding region of TGF-β-1, the side chain functionalities adopt approximately the same relative positioning when LIAEAK (SEQ ID NO:2) is in the conformation consistent with the φ, Ψ restrictions discussed. In particular, (1) Leu$_1$ of LLAEAK (SEQ ID NO:2) can act as a hydrophobic pharmacophore like Trp$_{52}$ of TGF-β1; (2) Ile$_2$ of LLAEAK (SEQ ID NO:2) can act like Ile$_{51}$ of TGF-β-1; (3) Ala$_5$ of LIAEAK (SEQ ID NO:2) can act like a portion of Leu, of TGF-0–1; and (4) Glu$_4$ of LIAEAK (SEQ ID NO:2) can act as a negatively-charged residue like Asp$_{55}$ of TGF-β-1. The only side-chain functional difference between LIAEAK (SEQ ID NO:2) and this corresponding region in TGF-β-1 is Ser$_{53}$.

Given the mobility of the TGF-β-1 side chains one can expect in an ensemble of NMR structures that the side chains of LIAEAK (SEQ ID NO:2) and this region of TGF-β-1 can adopt similar conformations when bound to a receptor.

It is to be understood that while the invention has been described above in conjunction with preferred specific embodiments, the description and examples are intended to illustrate and not limit the scope of the invention, which is defined by the scope of the appended claims.

It is claimed:

1. A pharmaceutical composition, comprising:
at least two components, one component being a TGF-β mimic having cellular proliferation inhibition activity, and being a six or seven amino acid peptide, having the sequence $AA_i$-$AA_{i+1}$-$AA_{i+2}$ as an initial sequence defining the N-terminus of said peptide or having the sequence Ala-$AA_i$-$AA_{i+1}$-$AA_{i+2}$, said peptide further having an $AA_{i+n}$ adjacent or proximal to said sequence in the C-terminus direction, wherein n is 3, 4, or 5 such that said peptide contains n−3 additional amino acid residues in between $AA_{i+2}$ and $AA_{i+n}$, and wherein
$AA_i$ is alanine, asparagine, or leucine,
$AA_{i+1}$ is valine, isoleucine, α-amino isobutyric acid, or α-amino butyric acid,
$AA_{i+2}$ is alanine or N-methyl alanine, and
$AA_{i+n}$ is glutamic acid, aspartic acid, glutamine, or asparagine, or other amino acid possessing a side-chain with a hydrogen bond acceptor, the other component being a collagen receptor ligand, said collagen receptor ligand having a domain including at least -Ile-Ala- folded in a β-bend at physiologic conditions; and
a physiologically acceptable carrier.

2. The pharmaceutical composition as in claim 1 wherein the collagen receptor ligand has enhanced cell binding with respect to collagen.

3. The pharmaceutical composition as in claim 1 wherein the collagen receptor ligand having a sequence selected from the group consisting of G-T-P-G-P-Q-G-I-A-G-Q-R-G-V-V (SEQ ID NO:17), G-P-Q-G-I-A-G-Q-R (SEQ ID NO:26), Q-G-I-A-G-Q (SEQ ID NO:27), Q-G-I-A-G-Q-R (SEQ ID NO: 28), F-G-I-A-G-F (SEQ ID NO:29), G-I-A-G-Q (SEQ ID NO:30), Q-G-A-I-A-Q (SEQ ID NO: 31), C-G-I-A-G-C (SEQ ID NO: 33), E-G-I-A-G-K (SEQ ID NO:34), (NAc)-I-A-A (SEQ ID NO:35), I-A-(βA) (SEQ ID NO:36), and (NAc)-I-A-(N-MeA) (SEQ ID NO:37).

4. The pharmaceutical composition as in claim 1 wherein the collagen receptor ligand has the sequence G-T-P-G-P-Q-G-I-A-G-Q-R-G-V-V (SEQ ID NO:17).

5. The pharmaceutical composition as in claim 1 wherein the TGF-β mimic has n=3 and the sequence further comprises $AA_{i+4}$-$AA_{i+5}$ wherein $AA_{i+4}$ and $AA_{i+5}$ are alanine.

6. The pharmaceutical composition as in claim 1 wherein the TGF-β mimic has n=4 and the amino acid residue in between $AA_{i+2}$ and $AA_{i+n}$ is proline or glycine.

7. The pharmaceutical composition as in claim 1 wherein the TGF-β mimic has n=5 and the two amino acid residues in between $AA_{i+2}$ and $AA_{i+n}$ are glycine.

8. The pharmaceutical composition as in claim 1 wherein the TGF-β mimic peptide is present in an amount of effective to inhibit cellular proliferation.

9. The pharmaceutical composition as in claim 8 wherein the TGF-β mimic is present in an amount effective to downregulate matrix metalloproteinase expression.

10. The pharmaceutical composition as in claim 9 wherein the TGF-β mimic has n=3 and the sequence further comprises $AA_{i+4}$-$AA_{i+5}$ wherein $AA_{i+4}$ and $AA_{i+5}$ are alanine.

11. The pharmaceutical composition as in claim 9 wherein the TGF-β mimic has n=4 and the amino acid residue in between $AA_{i+2}$ and $AA_{i+n}$ is proline or glycine.

12. The pharmaceutical composition as in claim 9 wherein the TGF-β mimic has n=5 and the two amino acid residues in between $AA_{i+2}$ and $AA_{i+n}$ are glycine.

13. The pharmaceutical composition as in claim 1 and wherein the TGF-β mimic is selected from the group consisting of A-N-V-A-E-N-A (SEQ ID NO: 1),
L-I-A-E-A-K (SEQ ID NO:2),
L-I-A-P-E-A (SEQ ID NO:3),
L-(Aib)-A-E-A-K (SEQ ID NO:4),
L-I-(Nme-A)-E-A-K (SEQ ID NO:5),
L-(Abu)-A-E-A-K (SEQ ID NO:6),
L-I-A-D-A-K (SEQ ID NO:9),
L-I-A-N-A-K (SEQ ID NO: 10),
L-I-A-E-A-A (SEQ ID NO: 11),
L-I-A-Q-A-K (SEQ ID NO: 12),
L-I-A-G-G-E (SEQ ID NO: 13),
L-I-A-G-E-G (SEQ ID NO: 14),
A-N-V-A-E-K (SEQ ID NO: 15),
L-I-A-K-G-K (SEQ ID NO: 16) and
L-(Abu)-A-E-A-K (SEQ ID NO: 19).

14. The pharmaceutical composition as in claim 13 wherein the collagen receptor ligand has enhanced cell binding with respect to collagen.

15. The pharmaceutical composition as in claim 1 wherein the collagen receptor ligand domain mimics collagen binding to cells.

16. The pharmaceutical composition as in claim 13 wherein each of the TGF-β mimic and the collagen receptor ligand is present in an amount effective to inhibit cell proliferation.

17. The pharmaceutical composition as in claim 13 wherein the collagen receptor ligand has the sequence G-T-P-G-P-Q-G-I-A-G-Q-R-G-V-V (SEQ ID NO:17).

18. A pharmaceutical composition comprising:

A-N-V-A-E-N-A (SEQ ID NO:1) and G-T-P-G-P-O-G-I-A-G-O-R-G-V-V (SEQ ID NO: 17) in a physiologically acceptable carrier.

19. A pharmaceutical composition, comprising:

at least two components, one component being a TGF-β mimic having cellular proliferation inhibition activity, and being a six or seven amino acid peptide, having the sequence $AA_i$-$AA_{i+1}$-$AA_{i+2}$ as an initial sequence defining the N-terminus of said peptide or having the sequence Ala-$AA_i$-$AA_{i+1}$-$AA_{i+2}$, said peptide further having an $AA_{i+n}$ adjacent or proximal to said sequence in the C-terminus direction, wherein n is 3, 4, or 5 such that said peptide contains n−3 additional amino acid residues in between $AA_{i+2}$ and $AA_{i+n}$, and wherein $AA_i$ is alanine, asparagine, or leucine, $AA_{i+1}$ is valine, isoleucine, α-amino isobutyric acid, or α-amino butyric acid, $AA_{i+2}$ is alanine or N-methyl alanine, and $AA_{i+n}$ is glutamic acid, aspartic acid, glutamine, or asparagine, or other amino acid possessing a side-chain with a hydrogen bond acceptor, the other component being a collagen receptor ligand, said collagen receptor ligand having a sequence selected from the group consisting of; G-T-P-G-P-Q-G-I-A-G-Q-R-G-V-V (SEQ ID NO:17), G-P-Q-G-I-A-G-Q-R (SEQ ID NO:26), Q-G-I-A-G-Q (SEQ ID NO:27), Q-G-I-A-G-Q-R(SEQ ID NO: 28), F-G-I-A-G-F (SEQ ID NO:29), G-I-A-G-Q (SEQ ID NO:30), Q-G-A-I-A-Q (SEQ ID NO: 31), C-G-I-A-G-C (SEQ ID NO: 33), E-G-I-A-G-K (SEQ ID NO:34), (NAc)-I-A-A (SEQ ID NO:35), I-A-(βA) (SEQ ID NO:36), and (NAc)-I-A-(N-MeA) (SEQ ID NO:37); and a physiologically acceptable carrier.

* * * * *